(12) United States Patent
Nikamoto

(10) Patent No.: US 9,233,857 B2
(45) Date of Patent: Jan. 12, 2016

(54) STERILIZATION DEVICE

(71) Applicant: NOK CORPORATION, Tokyo (JP)

(72) Inventor: Hiroyuki Nikamoto, Fujisawa (JP)

(73) Assignee: NOK CORPORATION, Tokyo (JP)

( * ) Notice: Subject to any disclaimer, the term of this patent is extended or adjusted under 35 U.S.C. 154(b) by 0 days.

(21) Appl. No.: 14/402,130

(22) PCT Filed: Apr. 25, 2013

(86) PCT No.: PCT/JP2013/062247
§ 371 (c)(1),
(2) Date: Nov. 19, 2014

(87) PCT Pub. No.: WO2013/175931
PCT Pub. Date: Nov. 28, 2013

(65) Prior Publication Data
US 2015/0129777 A1 May 14, 2015

(30) Foreign Application Priority Data

May 21, 2012 (JP) ................................ 2012-115880

(51) Int. Cl.
*A61L 2/10* (2006.01)
*C02F 1/32* (2006.01)
*A61L 9/20* (2006.01)

(52) U.S. Cl.
CPC . *C02F 1/325* (2013.01); *A61L 2/10* (2013.01); *A61L 9/20* (2013.01); *C02F 2201/009* (2013.01); *C02F 2201/3221* (2013.01); *C02F 2201/3222* (2013.01); *C02F 2201/3228* (2013.01)

(58) Field of Classification Search
USPC ................. 422/22, 24; 250/428, 432 R, 436, 250/453.11, 454.11, 455.11, 493.1, 504 R
See application file for complete search history.

(56) References Cited

U.S. PATENT DOCUMENTS

| 2007/0272877 | A1* | 11/2007 | Tribelsky | A61L 2/10 |
| | | | | 250/431 |
| 2008/0236183 | A1 | 10/2008 | Iimura | |
| 2012/0168641 | A1* | 7/2012 | Lizotte | 250/435 |
| 2012/0261319 | A1* | 10/2012 | Shinagawa | 210/170.03 |

FOREIGN PATENT DOCUMENTS

| JP | S63-144835 U | 9/1988 |
| JP | 2007-502200 A | 2/2007 |
| JP | 2007-139230 A | 6/2007 |
| JP | 2010-214241 A | 9/2010 |
| WO | 2005011753 A1 | 2/2005 |

* cited by examiner

*Primary Examiner* — Nicole Ippolito
(74) *Attorney, Agent, or Firm* — Harness, Dickey & Pierce, P.L.C.

(57) ABSTRACT

A sterilization device includes a housing having a flow passage R of a fluid that is to be sterilized; and an LED element being disposed in the housing to irradiate ultraviolet light into the flow passage R, wherein an inner wall surface of the flow passage has a pair of reflection surfaces (a first reflection surface and a second reflection surface) which directs the ultraviolet light irradiated from the LED element from one side of the flow passage R to another side thereof while reflecting the ultraviolet light a plurality of times; and a return surface that includes a surface that is perpendicular to an optical axis of the light which has been reflected a plurality of times from one side to the other side, and returns the light toward its original direction is formed on a side of the first reflection surface.

2 Claims, 9 Drawing Sheets (b)

STERILIZATION DEVICE

CROSS-REFERENCE TO RELATED APPLICATIONS

This application is a National Stage of International Application No. PCT/JP2013/062247, filed Apr. 25, 2013, which claims priority to Japanese Application No. 2012-115880, filed May 21, 2012. The entire disclosures of each of the above applications are incorporated herein by reference.

FIELD

The present disclosure relates to a sterilization device which sterilizes fluids such as liquid, gas, or the like.

BACKGROUND

In water purifiers or the like, there has been known one with a sterilization device that sterilizes water by irradiating ultraviolet light (refer to a first patent document). There has also been known a technology in which, when irradiating ultraviolet light into the interior of a flow passage, the irradiated light is caused to reflect repeatedly (refer to a second patent document).

With reference to FIG. 9, an imaginary technology in which, when ultraviolet light is irradiated into the interior of a flow passage, the irradiated light is reflected therein repeatedly and sterilizes a fluid such as water or the like will be explained. FIG. 9 is a schematic cross sectional view of a sterilization device according to such an imaginary technology.

A sterilization device 600 is provided with a housing 610 having a flow passage R for a fluid to be sterilized, and a light source unit 620 which is disposed in the housing 610. The light source unit 620 is provided with a LED element 621 which is a light source for irradiating ultraviolet light into the flow passage R. An inner wall surface of the flow passage R has a pair of reflection surfaces 611, 612 which direct the ultraviolet light irradiated from the LED element 621 from one side to another side of the flow passage R while reflecting the ultraviolet light a plurality of times. Note that a line L in FIG. 9 indicates the center (optical axis) of the ultraviolet light irradiated from the LED element 621.

Beneath the cross sectional view shown in FIG. 9, a relation between the distance and the light intensity along the centerline of the flow passage R from the one side to the other side is illustrated in a graph. As illustrated, the light intensity attenuates as being inversely proportional to the square of the distance. In the example as illustrated, when the ultraviolet light leaks to the outside of the housing 610, the light intensity thereof is reduced to such a degree that it does not affect human bodies or the like. Here, in order to achieve a sterilization effect, the light intensity needs to be equal to or greater than a certain value. As the fixed value varies with the wavelength of the ultraviolet light, the light intensity required to achieve the sterilization effect with the ultraviolet light irradiated from the LED element 621 is shown as Y0 [J/cm$^2$]. In this case, the sterilization effect will be achieved only in a region within a distance up to X0 [mm].

As described, the light intensity of the ultraviolet light attenuates as being inversely proportional to the square of the distance. For that reason, in the case of the above described imaginary technology, there is a problem that the region in which a sterilization effect can be achieved is narrow, and thus sterilization efficiency is low. On the other hand, there is yet another problem that in order to keep human bodies or the like from being affected when the ultraviolet light leaks to the outside, the overall length of the housing 610 needs to be constructed much longer than the length of the region in which the sterilization effect can be achieved. Meanwhile, the ultraviolet light not only causes bad influences to human bodies, but in cases where the sterilization device 600 is attached to a water purifier or the like, it also causes deterioration of other components that constitute the water purifier or the like.

CITATION LIST

Patent Literature

Japanese patent application laid-open No. 2010-214241
Published Japanese Translation No. 2007-502200 of PCT International Publication

SUMMARY

Technical Problem

The object of the present disclosure is to provide a sterilization device which is intended to improve sterilization efficiency, while being reduced in size.

Solution to Problem

In order to solve the above described problems, the present disclosure employs the following means.

A sterilization device according to the present disclosure that comprises: a housing having a flow passage of a fluid that is to be sterilized; and a light source being disposed in the housing to irradiate ultraviolet light into the flow passage, is characterized in that an inner wall surface of the flow passage has a pair of reflection surfaces (e.g. mirrors) which direct the ultraviolet light irradiated from the light source from one side of the flow passage to another side thereof while reflecting the ultraviolet light a plurality of times; and a return surface that is composed of a surface that is perpendicular to an optical axis of the light which has been reflected a plurality of times from the one side to the other side, and returns the light toward its original direction is formed on a side of one of the pair of reflection surfaces.

According to the present disclosure, after being reflected a plurality of times by the pair of reflection surfaces while traveling from the one side to the other side of the flow passage, the ultraviolet light is returned by the return surface and travels from the other side to the one side of the flow passage while being reflected a plurality of times. Accordingly, the light intensity of the ultraviolet light passing through the interior of the flow passage becomes the sum of the light intensity of the ultraviolet light that travels from the one side to the other side of the flow passage, and the light intensity of the ultraviolet light that travels from the other side to the one side of the flow passage. Therefore, the light intensity of the ultraviolet light passing through the interior of the flow passage can be enhanced. As a result, it becomes possible to broaden a region in which a sterilization effect can be achieved. In addition, because the ultraviolet light traveling from the one side to the other side of the flow passage can be returned by the return surface, it is possible to suppress the ultraviolet light from leaking to outside of the housing. In accordance with this, it is no longer necessary to increase the overall length of the housing in order to keep the light intensity of the ultraviolet light from affecting human bodies or the like, and hence, the housing can be reduced in size.

As for the pair of reflection surfaces, each surface can be composed of a plane and can be constructed such that the planes are arranged in parallel with each other and are opposing each other. In a case of employing this construction, the following configurations, for example, can be employed for a geometrical configuration of the light source and so on to direct the ultraviolet light irradiated from the light source from the one side to the other side of the flow passage while reflecting it a plurality of times.

Firstly, a configuration in which the light source is arranged with respect to the housing in such a manner that the direction of the ultraviolet light irradiated from the light source can be inclined from the one side toward the other side of the flow passage with respect to the normal line of the reflection surfaces can be employed.

Secondly, a configuration in which the light source is arranged on the housing in such a manner that the direction of the ultraviolet light irradiated from the light source coincides with the normal line of the reflection surfaces, and in which a preliminary reflection surface to reflect the ultraviolet light irradiated from the light source to incline the light toward the other side of the flow passage is disposed on a side that is further to the one side of the flow passage from the pair of reflection surfaces can be employed. Even in this configuration, after reflecting the ultraviolet light irradiated from the light source by preliminary reflection surface, it is possible to let the light travel from the one side to the other side of the flow passage by reflecting it a plurality of times by the pair of reflection planes.

In addition, at a location where the ultraviolet light irradiated from the light source enters the flow passage, a window that prevents an incursion of the fluid while it allows the ultraviolet light to pass through may be provided so that the fluid to be sterilized does not flow toward the light source side. In this case, it is desirable not to let the reflected light, that is the ultraviolet light irradiated from the light source and reflected for the first time, enter the window. This is because a portion of the reflected light which enters the window does not thereafter return to the interior of the flow passage, and thus it does not contribute to sterilization. Hence, the sterilization efficiency will be decreased.

As a measure to deal with this, a half mirror which allows the ultraviolet light traveling from the light source side toward the interior of the flow passage to pass through, while reflecting the ultraviolet light traveling from the interior of the flow passage toward the light source side, can be provided to the window. Nevertheless, because the transmittance and the reflectance of the half mirror are low as compared with ordinary mirrors, the amount of light transmitting therethrough is reduced. Hence, it is desirable to keep the reflected light from entering the window by a geometrical configuration of the light source and/or a preliminary reflection surface. When, however, the direction of the ultraviolet light irradiated from the light source and/or the direction of the ultraviolet light reflected by the preliminary reflection surface is inclined too much toward the other side of the flow passage, the distance the light travels after being reflected once and until the next reflection may become long. In this case, a region through which the ultraviolet light does not pass may be formed (increased) within the flow passage. As a measure to deal with this, for example, a reflection direction regulating surface to regulate the direction of the reflected light of the ultraviolet light can be provided on one of the pair of reflection surfaces.

Here, note that the above described respective constructions can be combined with one another wherever possible.

Advantageous Effects of Disclosure

As explained above, according to the present disclosure, an improvement in sterilization efficiency can be achieved, while attaining reduction in size.

DRAWINGS

DETAILED DESCRIPTION

Hereinafter, modes for carrying out the present disclosure will be described in detail by way of example based on embodiments thereof with reference to the attached drawings. However, the dimensions, materials, shapes, relative arrangements and so on of component parts described in the embodiments are not intended to limit the scope of the present disclosure to these alone in particular as long as there are no specific statements.

(Application Example of Sterilization Device)

A sterilization device according to an embodiment can be applied to various kinds of uses such as sterilizing liquids like water (tap water) and/or gases like air. In the case of the former, the sterilization device can be, for example, fitted to a pot-type water purifier, attached to a faucet of a water tap, or disposed in a water purifier attached to a water tap for sterilizing water. In addition, in the case of the latter, the sterilization device can be, for example, attached to an emission gas pipe to sterilize emission gas. Here, reference will be made, by way of example, to a case where a cartridge-type sterilization device is fitted to a pot-type water purifier, with reference to FIG. 1.

Figure 1:
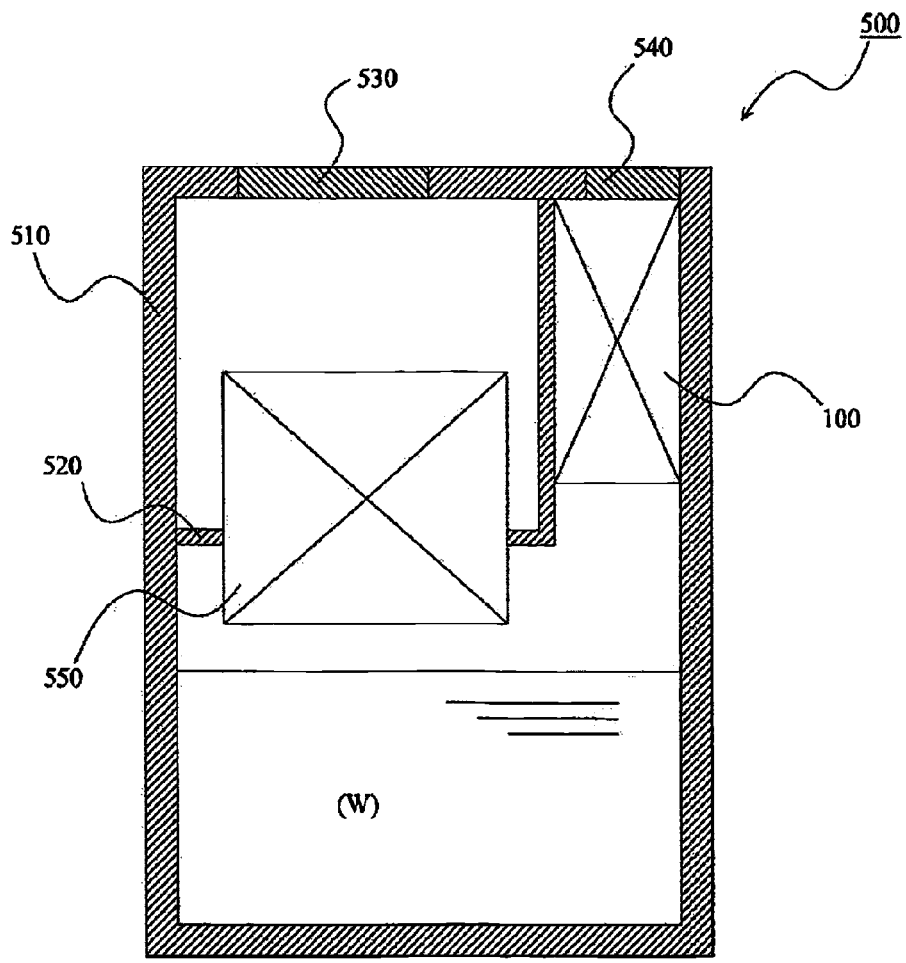
FIG. 1 is a schematic construction view of a water purifier provided with a sterilization device according to an embodiment of the present disclosure.

The pot-type water purifier 500 shown in FIG. 1 is provided with a case 510, a partition 520 which divides a space inside the case 510 into two regions, and a water-purifying cartridge 550 fitted to the partition 520. In addition, in an upper portion of the case 510, a first lid 530 for pouring raw water such as tap water into the case 510, and a second lid 540 for ejecting the purified water to outside are provided. The interior of the water-purifying cartridge 550 is filled up with activated carbon.

According to the water purifier 500 constructed as described above, when raw water is poured into the case 510 with the first lid 530 open, water W purified by the water-purifying cartridge 550 is stored in a lower portion of the case 510. Then, the purified water W can be ejected to outside by leaning the case 510 to the side of the second lid 540, with the second lid 540 open.

Here, in the case of the water purifier 500 constructed as described above, chlorine in the water stored in the case 510 has been removed by the activated carbon. For that reason, there is a problem that in case the water is left for a long period of time, bacteria may occur. Accordingly, in the water purifier 500 according to this embodiment, in order to sterilize the stored water W, the sterilization device 100 of the cartridge-type is fitted in the vicinity of the second lid 540. By doing so, when the purified water W that has been stored is ejected to the outside of the case 510, the water W is sterilized by ultraviolet light at the time of passing through a flow passage inside the sterilization device 100.

First Embodiment

Figure 2:
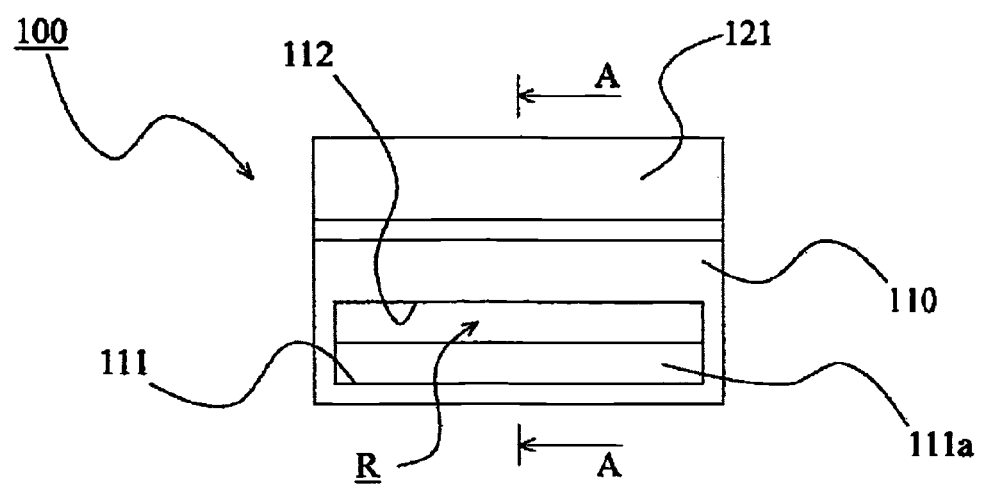
FIG. 2 is a front view of a sterilization device according to a first embodiment of the present disclosure.
Figure 3:
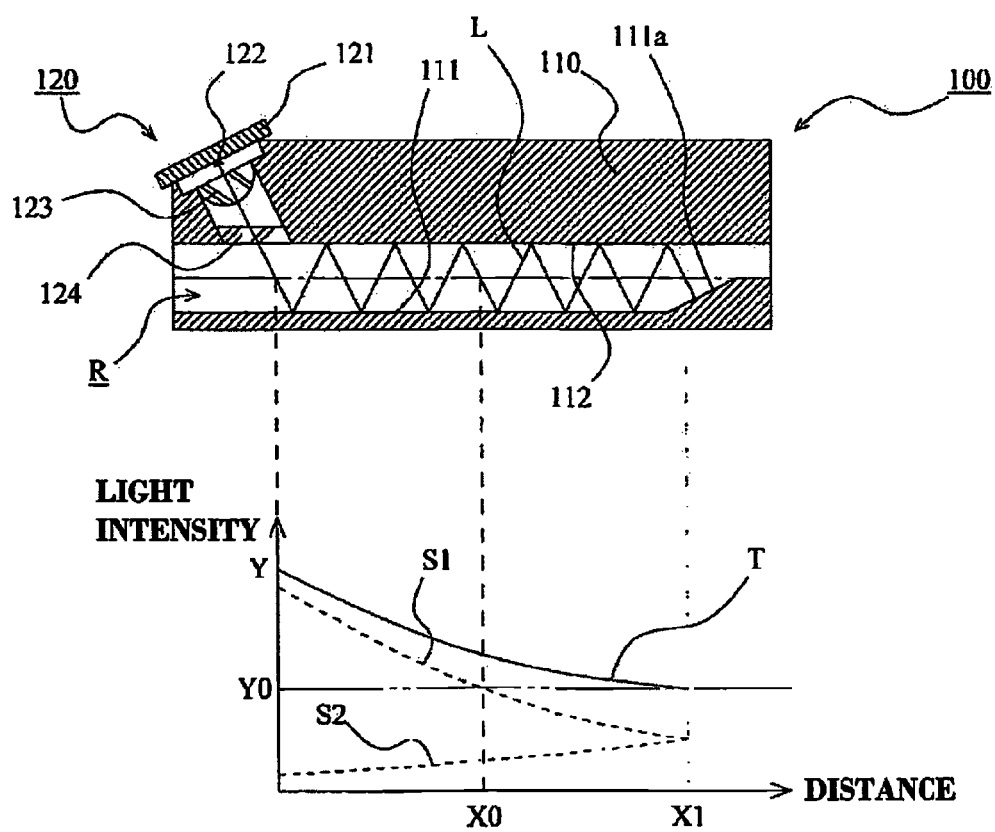
FIG. 3 is a schematic cross sectional view of the sterilization device according to the first embodiment of the present disclosure.

A sterilization device according to a first embodiment of the present disclosure will be explained, with reference to FIG. 2 and FIG. 3. FIG. 2 is a front view of the sterilization device according to the first embodiment of the present disclosure. FIG. 3 is a schematic cross sectional view (A-A cross sectional view in FIG. 2) of the sterilization device according to the first embodiment of the present disclosure. In FIG. 3, a relation between the distance and the light intensity along the centerline of a flow passage R from one side to another is illustrated in a graph beneath the cross sectional view.

The sterilization device 100 is provided with a housing 110 having the flow passage R of a fluid that is to be sterilized (in this case water), and a light source unit 120 being disposed in the housing 110.

The light source unit 120 is provided with a substrate board 121, an LED element 122 mounted on the substrate board 121, and a lens 123 for condensing ultraviolet light irradiated from the LED element 122. The LED element 122 is a light source for irradiating the ultraviolet light into the flow passage R. The number of the LED element 122 is not limited in particular, and multiple elements can be arranged in a row along a longitudinal direction of the substrate board 121 (i.e. a width direction of the housing 110). With respect to a power supply (battery) for the LED element 122, it may be disposed in the sterilization device 100 (e.g. the housing 110), or may be disposed on the outside of the sterilization device 100 (e.g. the case 510 of the above described water purifier 500).

In addition, a window 124 is disposed between the light source unit 120 and the flow passage R. The window 124 is arranged so as to separate a region in which the light source unit 120 is disposed from the flow passage R. That is, in order to keep the fluid to be sterilized (water) from flowing toward the side of the light source unit 120, the window 124 bears a role to prevent an incursion of the fluid into the side of the light source unit 120 while allowing the ultraviolet light to pass through.

As shown in FIG. 2, the flow passage R formed in the housing 110 is constructed such that its cross section becomes a rectangle. As shown in FIG. 3, an inner wall surface of the flow passage R has a pair of reflection surfaces which direct the ultraviolet light irradiated from the LED element 122 from the one side of the flow passage R to the other side thereof while reflecting the ultraviolet light a plurality of times. In the following, for the purpose of explanation, the pair of reflection surfaces are referred to as a first reflection surface 111 and a second reflection surface 112, respectively, where necessary. Note that a line L in FIG. 3 indicates the center (optical axis) of the ultraviolet light irradiated from the LED element 122.

The first reflection surface 111 and the second reflection surface 112 are each composed of a plane, and are constructed such that the planes are arranged in parallel with each other and are opposing each other. As shown in FIG. 3, the LED element 122 (the light source unit 120) is arranged with respect to the housing 110 in such a manner that the direction of the ultraviolet light irradiated from the LED element 122 inclines from the one side toward the other side of the flow passage R with respect to the normal line of the first reflection surface 111 and the second reflection surface 112.

Then, in this embodiment, on the side of the first reflection plane 111, a return surface 111a is formed on a side that is further to the other side of the flow passage R from the first reflection surface 111. The return surface 111a is composed of a surface that is perpendicular to the optical axis of the light which has been reflected a plurality of times from the one side to the other side of the flow passage R. Accordingly, the light that has been reflected a plurality of times is returned toward its original direction by the return surface 111a.

As shown in the graph in FIG. 3, the light intensity attenuates as being inversely proportional to the square of the distance. Note that, in the drawing, a dotted line S1 represents the light intensity of the ultraviolet light traveling from the one side to the other side of the flow passage R, and a dotted line S2 represents the light intensity of the ultraviolet light traveling from the other side toward the one side of the flow passage R after being turned back by the return surface 111a. In addition, a solid line T represents the light intensity of the ultraviolet light passing in the flow passage R (namely, a sum of S1 and S2).

As already explained in Background Art, in order to achieve a sterilization effect, it is necessary for the light intensity to be equal to or greater than a certain value. In this embodiment, similar to the above described imaginary technology, the light intensity required to achieve the sterilization effect with the ultraviolet light irradiated from the LED element 122 is shown as Y0 [J/cm$^2$]. In the case of a construction in which the return surface 111a is not provided, the light intensity is as shown by the dotted line S1, and a sterilization effect will be achieved only in a region up to a distance of X0 [mm]. In contrast to this, in this embodiment, the return surface 111a is arranged in the vicinity where the light intensity becomes a half of Y0. As a result of this, in the case of this embodiment, as can be seen from the solid line T, a sterilization effect can be achieved in a region up to a distance of X1 (>X0) [mm] at which the return surface 111a is disposed.

In addition, as can be seen from the dotted line S2, the light intensity of the ultraviolet light traveling from the other side to the one side of the flow passage R becomes sufficiently low in the vicinity of the light source unit 120. Moreover, the ultraviolet light traveling toward the one side of the flow passage R enters the side of the light source unit 120 through the window 124. Accordingly, almost no ultraviolet light leaks to the outside of the housing 110.

Advantages of the Sterilization Device According to the Embodiment

According to the sterilization device 100 of this embodiment, after being reflected a plurality of times by the first reflection surface 111 and the second reflection surface 112 while traveling from the one side to the other side of the flow passage R, the ultraviolet light is returned by the return surface 111a and travels from the other side to the one side of the flow passage R while being reflected a plurality of times.

Accordingly, the light intensity of the ultraviolet light passing through the interior of the flow passage becomes the sum (the solid line T in the graph of FIG. 3) of the light intensity of the ultraviolet light that travels from the one side to the other side of the flow passage R (the dotted line S1 in the same graph), and the light intensity of the ultraviolet light that travels from the other side to the one side of the flow passage R (the dotted line S2 in the same graph). Therefore, the light intensity of the ultraviolet light passing through the interior of the flow passage R can be enhanced. As a result, it becomes possible to broaden a region in which a sterilization effect can be achieved. In addition, because the ultraviolet light traveling from the one side to the other side of the flow passage R can be returned by the return surface 111a, it is possible to suppress the ultraviolet light from leaking to outside of the housing 110. In accordance with this, it is no longer necessary to increase the overall length of the housing 110 in order to keep the light intensity of the ultraviolet light from affecting human bodies or the like, and hence, the housing 110 can be reduced in size. Moreover, it is possible to suppress the ultraviolet light from leaking to outside of the housing 110, thus in cases where the sterilization device 100 is used for the above described water purifier 500, deterioration of the case 510 and the like can be suppressed.

Note that the direction of the fluid flowing in the interior of the flow passage R is not limited in particular, thus for example, the fluid may flow from the left side to the right side in FIG. 3, or may flow from the right side to the left side.

Second Embodiment

Figure 4:
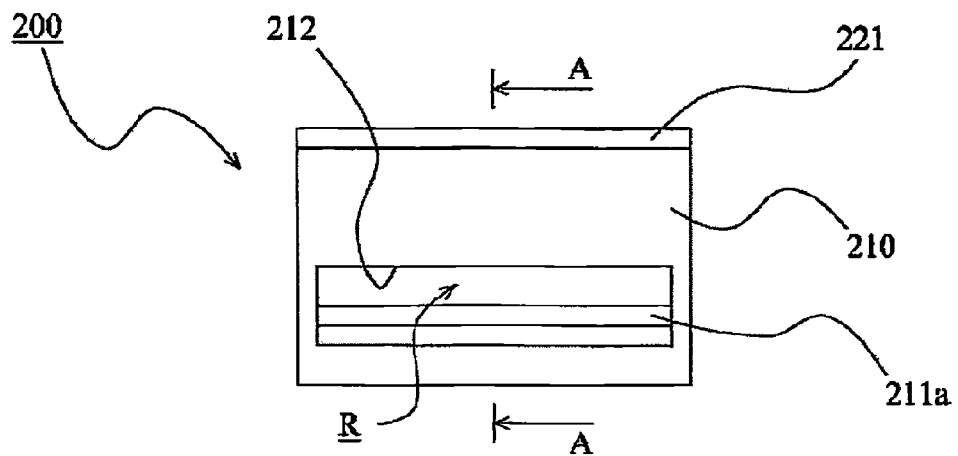
FIG. 4 is a front view of a sterilization device according to a second embodiment of the present disclosure.
Figure 5:
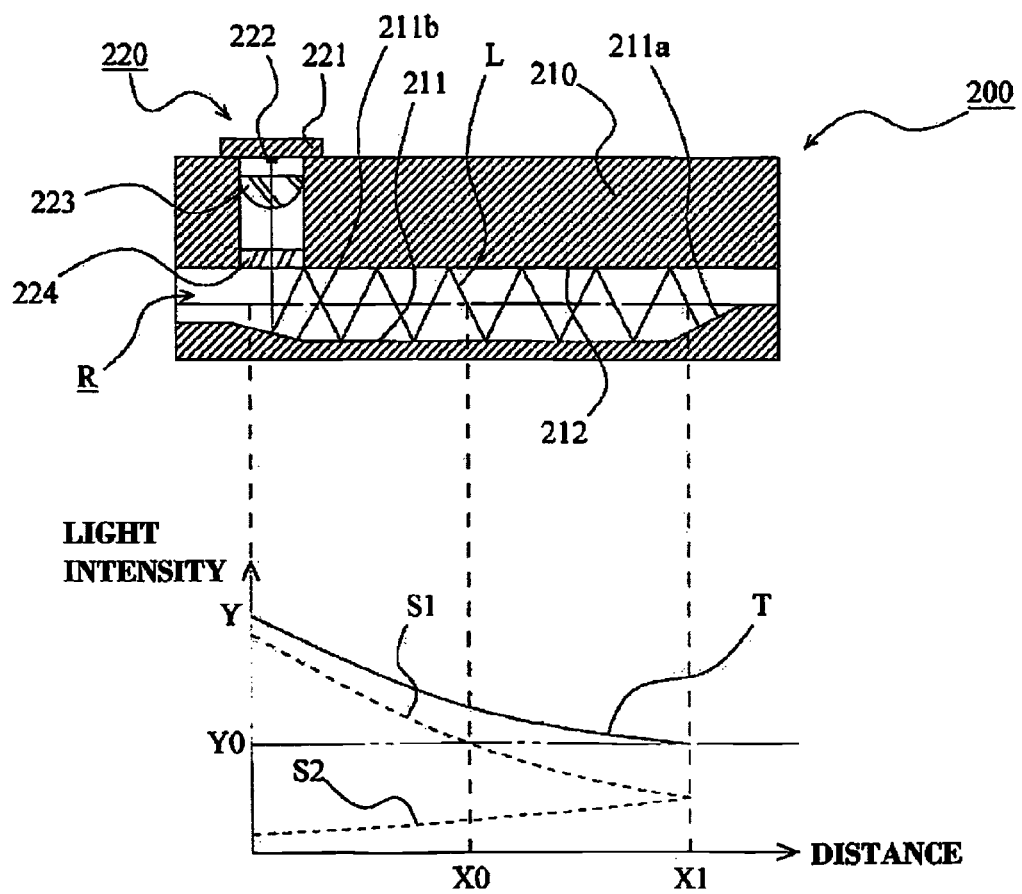
FIG. 5 is a schematic cross sectional view of the sterilization device according to the second embodiment of the present disclosure.

A second embodiment of the present disclosure is shown in FIG. 4 and FIG. 5. FIG. 4 is a front view of a sterilization device according to the second embodiment of the present disclosure. FIG. 5 is a schematic cross sectional view (A-A cross sectional view in FIG. 4) of the sterilization device according to the second embodiment of the present disclosure. In FIG. 5, a relation between the distance and the light intensity along the centerline of a flow passage R from one side to another is illustrated in a graph beneath the cross sectional view. In addition, as for an example of the application of a sterilization device 200 according to this embodiment, it is similar to the one already described with reference to FIG. 1.

The sterilization device 200 is provided with a housing 210 having a flow passage R for a fluid that is to be sterilized and a light source unit 220 being disposed in the housing 210.

The light source unit 220 is provided with a substrate board 221, an LED element 222 mounted on the substrate board 221, and a lens 223 for condensing ultraviolet light irradiated from the LED element 222. The LED element 222 is a light source for irradiating the ultraviolet light into the flow passage R. The number of the LED element 222 is not limited in particular, and multiple elements can be arranged in a row along a longitudinal direction of the substrate board 221 (i.e. a width direction of the housing 210). With respect to a power supply (battery) for the LED element 222, it may be disposed in the sterilization device 200 (e.g. the housing 210), or may be disposed on the outside of the sterilization device 200 (e.g. the case 510 of the above described water purifier 500).

In addition, a window 224 is disposed between the light source unit 220 and the flow passage R. The window 224 is arranged so as to separate a region in which the light source unit 220 is disposed from the flow passage R. That is, in order to keep the fluid to be sterilized (water) from flowing toward the side of the light source unit 220, the window 224 bears a role to prevent an incursion of the fluid into the side of the light source unit 220 while allowing the ultraviolet light to pass through.

As shown in FIG. 4, the flow passage R formed in the housing 210 is constructed such that its cross section becomes a rectangle. As shown in FIG. 5, an inner wall surface of the flow passage R has a pair of reflection surfaces which direct the ultraviolet light irradiated from the LED element 222 from the one side of the flow passage R to the other side thereof while reflecting the ultraviolet light a plurality of times. In the following, for the purpose of explanation, the pair of reflection surfaces are referred to as a first reflection surface 211 and a second reflection surface 212, respectively, where necessary. Note that a line L in FIG. 5 indicates the center (optical axis) of the ultraviolet light irradiated from the LED element 222.

The first reflection surface 211 and the second reflection surface 212 are each composed of a plane, and are constructed such that the planes are arranged in parallel with each other and are opposing each other. As shown in FIG. 5, the LED element 222 (the light source unit 220) is arranged with respect to the housing 210 in such a manner that the direction of the ultraviolet light irradiated from the LED element 222 coincides with the normal line of the first reflection surface 211 and the second reflection surface 212.

Then, in this embodiment too, as in the first embodiment, on the side of the first reflection plane 211, a return surface 211a is formed on a side that is further to the other side of the flow passage R from the first reflection surface 211. The return surface 211a is composed of a surface that is perpendicular to the optical axis of the light which has been reflected a plurality of times from the one side to the other side of the flow passage R. Accordingly, the light that has been reflected a plurality of times is returned toward its original direction by the return surface 211a.

Then, in this embodiment, a preliminary reflection surface 211b to reflect the ultraviolet light irradiated from the LED element 222 so that the light inclines toward the other side of the flow passage is formed on a side that is further to the one side of the flow passage R from the first reflection surface 211. By providing the preliminary reflection surface 211b, after the ultraviolet light irradiated from the LED element 222 is reflected by the preliminary reflection surface 211b, the light path of the ultraviolet light becomes similar to that in the above described first embodiment. Accordingly, as shown in the graph in FIG. 5, the relation between the distance and the light intensity becomes similar to that in the case of the first embodiment (the graph in FIG. 3).

As described above, in the sterilization device 200 according to this embodiment too, the same effects as in the case of the sterilization device 100 according to the above described first embodiment can be achieved. In addition, in the case of the sterilization device 100 according to the above described first embodiment, the construction is such that the light source unit 120 is disposed aslant with respect to the housing 110, but on the other hand, in the case of the sterilization device 200 according to this embodiment, there is no need for the light source unit 220 to be disposed aslant with respect to the housing 210, so it has an advantage that the device as a whole can be reduced more in size.

Figure 6A:
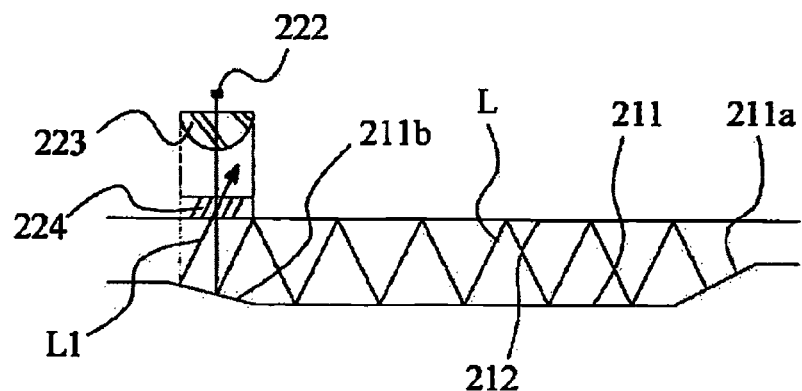
FIG. 6A and FIG. 6B are views explaining disadvantageous points of the sterilization device according to the second embodiment of the present disclosure.
Figure 6B:
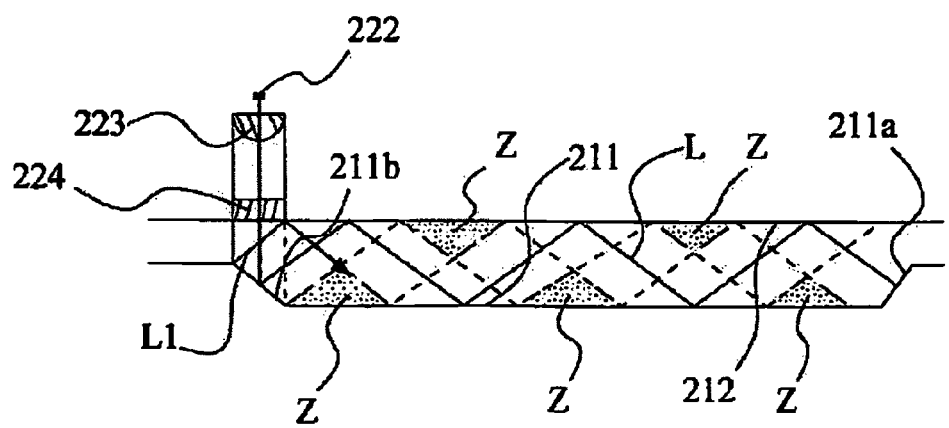

Referring to FIG. 6A and FIG. 6B, a case where the sterilization device according to this embodiment can be disadvantageous will be explained.

As described above, the window 224 is disposed between the light source unit 220 and the flow passage R. Here, it is desirable not to let the reflected light, that is the ultraviolet light irradiated from the LED element 222 and reflected for the first time, enter the window 224. This is because a portion of the reflected light which enters the window 224 does not thereafter return to the interior of the flow passage R and thus it does not contribute to sterilization. Hence, the sterilization efficiency will be decreased.

As to the ultraviolet light irradiated from the LED element 222, FIG. 6A shows a case where although its central portion (optical axis) is being reflected by the second reflection surface 212 and is not entering the window 224, a portion of the ultraviolet light is entering the window 224 (refer to a line L1). In this example, almost a half of the ultraviolet light irradiated from the LED element 222 is entering the window 224.

As a measure to deal with this, a half mirror which allows the ultraviolet light traveling from the LED element 222 side toward the interior of the flow passage R to pass through, while reflecting the ultraviolet light traveling from the interior of the flow passage R toward the LED element 222 side, can be provided to the window 224. For example, a half mirror treatment in which a thin metal film is vapor deposited on the surface of the window 224 composed of glass can be applied. Nevertheless, because the transmittance and the reflectance of the half mirror are low as compared with ordinary mirrors, the amount of light transmitting therethrough is reduced. Hence, it is desirable to keep the reflected light from entering the window 224 by a geometrical configuration of each component.

For example, by extending the distance from the window 224 to the preliminary reflection surface 211b, it is possible to keep the reflected light from entering the window 224. However, in this case, there is a disadvantage that the distance between the first reflection surface 211 and the second reflection surface 212 becomes long, causing the housing 210 to become large, and hence difficulties in reducing in size may arise.

In addition, by increasing the gradient of the preliminary reflection surface 211b, it is possible to keep the reflected light from entering the window 224. However, in this case, the distance the light travels after being reflected once and until the next reflection may become long. Thus, a region through which the ultraviolet light does not pass may be formed (increased) within the flow passage R. This point will be described below in more detail with reference to FIG. 6B.

As shown in FIG. 6B, by increasing the gradient of the preliminary reflection surface 211b, it is possible to keep the reflected light from entering the window 224, without extending the distance from the window 224 to the preliminary reflection surface 211b. Note that in FIG. 6B, a line L1 indicates a light path that is the closest to the one side of the flow passage R.

However, in this case, both the distance the ultraviolet light travels after it is reflected by the first reflection surface 211 until it reaches the second reflection surface 212 (the distance in the direction from the one side to the other side of the flow passage R), and the distance it travels after it is reflected by the second reflection surface 212 until it reaches the first reflection surface 211 become long. As a result, a region Z through which the ultraviolet light does not pass may be formed within the flow passage R. Accordingly, this becomes a cause to decrease the sterilization efficiency. Next, reference will be made to an embodiment in which such a defect can be eliminated.

Third Embodiment

Figure 7:
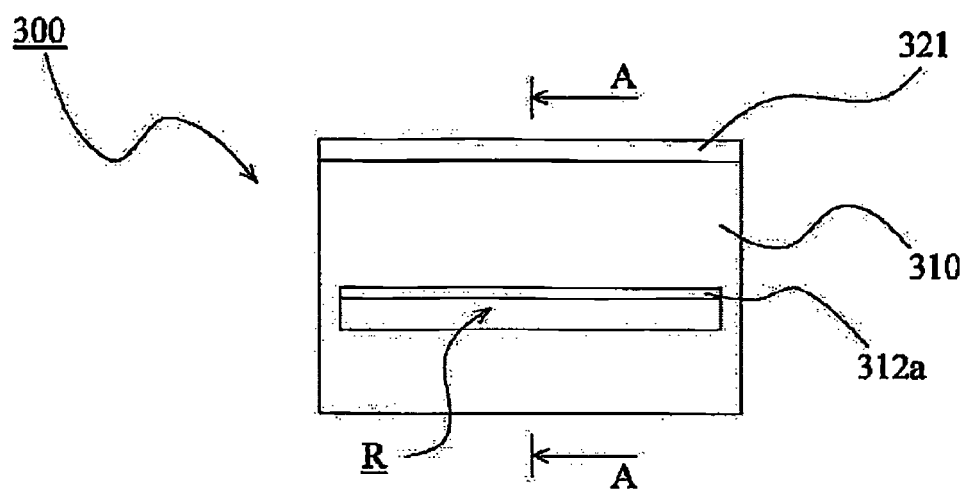
FIG. 7 is a front view of a sterilization device according to a third embodiment of the present disclosure.
Figure 8:
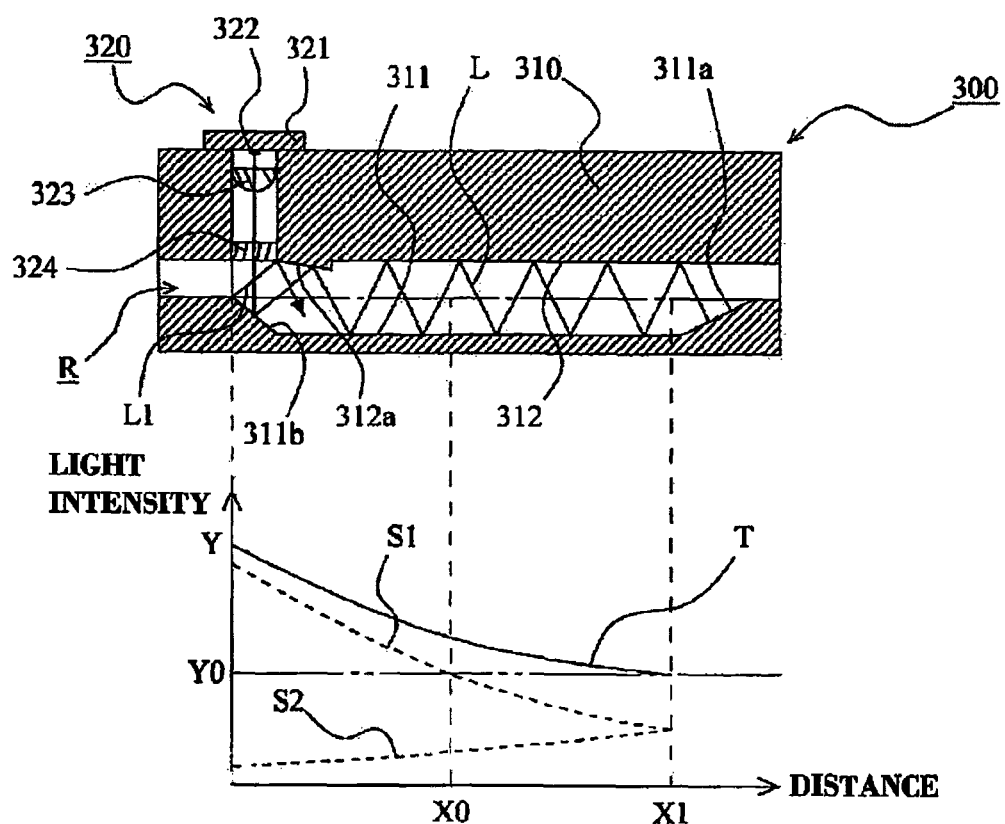
FIG. 8 is a schematic cross sectional view of the sterilization device according to the third embodiment of the present disclosure.
Figure 9:
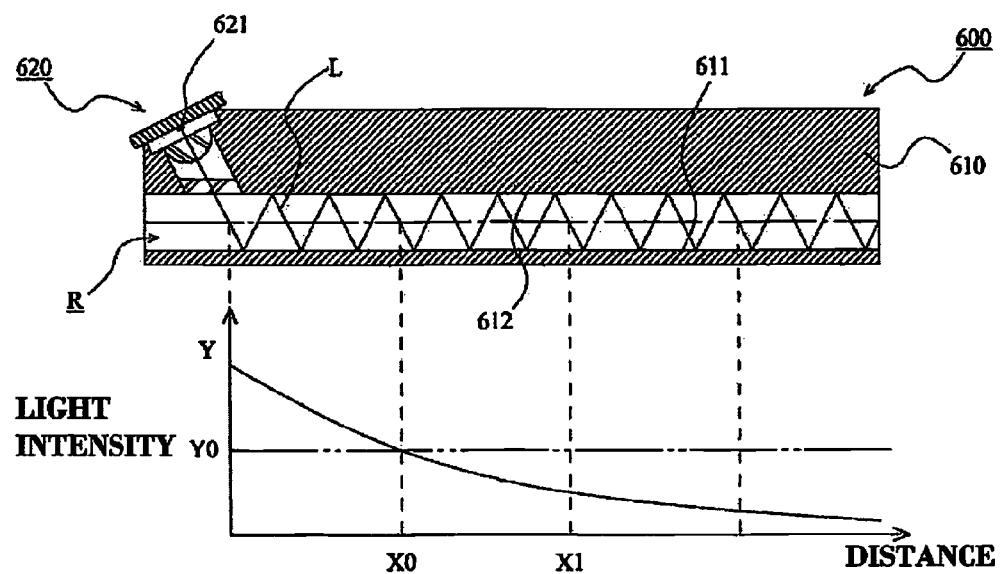
FIG. 9 is a schematic cross sectional view of a sterilization device according to an imaginary technology.

A third embodiment of the present disclosure is shown in FIG. 7 and FIG. 8. FIG. 7 is a front view of a sterilization device according to the third embodiment of the present disclosure. FIG. 8 is a schematic cross sectional view (A-A cross sectional view in FIG. 7) of the sterilization device according to the third embodiment of the present disclosure. In FIG. 8, a relation between the distance and the light intensity along the centerline of a flow passage R from one side to another is illustrated in a graph beneath the cross sectional view. In addition, as for an example of the application of a sterilization device 300 according to this embodiment, it is similar to the one already described with reference to FIG. 1.

The sterilization device 300 is provided with a housing 310 having a flow passage R for a fluid that is to be sterilized and a light source unit 320 being disposed in the housing 310.

The light source unit 320 is provided with a substrate board 321, an LED element 322 mounted on the substrate board 321, and a lens 323 for condensing ultraviolet light irradiated from the LED element 322. The LED element 322 is a light source for irradiating the ultraviolet light into the flow passage R. The number of the LED element 322 is not limited in particular, and multiple elements can be arranged in a row along a longitudinal direction of the substrate board 321 (i.e. a width direction of the housing 310). With respect to a power supply (battery) for the LED element 322, it may be disposed in the sterilization device 300 (e.g. the housing 310), or may be disposed on the outside of the sterilization device 300 (e.g. the case 510 of the above described water purifier 500).

In addition, a window 324 is disposed between the light source unit 320 and the flow passage R. The window 324 is arranged so as to separate a region in which the light source unit 320 is disposed from the flow passage R. That is, in order to keep the fluid to be sterilized (water) from flowing toward the side of the light source unit 320, the window 324 bears a role to prevent an incursion of the fluid into the side of the light source unit 320 while allowing the ultraviolet light to pass through.

As shown in FIG. 7, the flow passage R formed in the housing 310 is constructed such that its cross section becomes a rectangle. As shown in FIG. 8, an inner wall surface of the flow passage R has a pair of reflection surfaces which direct the ultraviolet light irradiated from the LED element 322 from one side of the flow passage R to the other side thereof while reflecting the ultraviolet light a plurality of times. In the following, for the purpose of explanation, the pair of reflection surfaces are referred to as a first reflection surface 311 and a second reflection surface 312, respectively, where necessary. Note that a line L in FIG. 8 indicates the center (optical axis) of the ultraviolet light irradiated from the LED element 322.

The first reflection surface 311 and the second reflection surface 312 are each composed of a plane, and are constructed such that the planes are arranged in parallel with each other and are opposing each other. As shown in FIG. 8, the LED element 322 (the light source unit 320) is arranged with respect to the housing 310 in such a manner that the direction of the ultraviolet light irradiated from the LED element 322 coincides with the normal line of the first reflection surface 311 and the second reflection surface 312.

Then, in this embodiment too, as in the first embodiment, on the side of the first reflection plane 311, a return surface 311a is formed on a side that is further to the other side of the flow passage R from the first reflection surface 311. The return surface 311a is composed of a surface that is perpendicular to the optical axis of the light which has been reflected a plurality of times from the one side to the other side of the flow passage R. Accordingly, the light that has been reflected a plurality of times is returned toward its original direction by the return surface 311a.

Moreover, in this embodiment, as in the second embodiment, a preliminary reflection surface 311b to reflect the ultraviolet light irradiated from the LED element 322 so that the light inclines toward the other side of the flow passage is formed on a side that is further to the one side of the flow passage R from the first reflection surface 311. The preliminary reflection surface 311b is formed at a steep angle so as to keep the reflected light of the ultraviolet light irradiated from the LED element 322 from entering the window 324. Note that in FIG. 8, a line L1 indicates a light path that is the closest to the one side of the flow passage R.

Then, in the case of this embodiment, a reflection direction regulating surface 312a to regulate the direction of the reflected light of the ultraviolet light is formed on a side that is further to the one side of the flow passage R from the second reflection surface 312. By providing the reflection direction regulating surface 312a, after the ultraviolet light irradiated from the LED element 322 is reflected by the preliminary reflection surface 311b and further reflected by the reflection direction regulating surface 312a, the light path of the ultraviolet light becomes similar to that in the above described first embodiment. Accordingly, as shown in the graph in FIG. 8, the relation between the distance and the light intensity becomes similar to that in the case of the first embodiment (the graph in FIG. 3).

As described above, in the sterilization device 300 according to this embodiment too, the same effects as in the case of the sterilization device 100 according to the above described first embodiment can be achieved. In addition, in the case of the sterilization device 100 according to the above described first embodiment, the construction is such that the light source unit 120 is disposed aslant with respect to the housing 110, but on the other hand, in the case of the sterilization device 300 according to this embodiment, similar to the case of the second embodiment, there is no need for the light source unit 320 to be disposed aslant with respect to the housing 310, so it has an advantage that the device as a whole can be reduced more in size.

Note that in this embodiment, a construction in which the reflection direction regulating surface is further added to the construction shown in the above described second embodiment has been shown. In addition, by employing such a construction, it becomes possible to keep the first-reflected light among the ultraviolet light irradiated from the LED element from entering the window, and at the same time, it becomes possible to eliminate (reduce) a region in the light path through which the ultraviolet light does not pass. Nevertheless, also in the construction shown in the above described first embodiment, depending on the direction of the light source unit (the LED element), there is a possibility that a region in the light path through which the ultraviolet light does not pass may exist (increase). Accordingly, in such a case, by providing a reflection direction regulating surface, as shown in this embodiment, to the construction shown in the first embodiment, it also becomes possible to regulate the light path, thereby eliminating (reducing) the region in the light path through which the ultraviolet light do not pass.

As to the LED element as shown in each of the above described embodiments, it is preferable to make the LED element irradiate ultraviolet light only at the time of using by providing, for example, an on-off switch.

REFERENCE SIGNS LIST 100, 200, 300 sealing device
110, 210, 310 housing
111, 211, 311 first reflection surface
111a, 211a, 311a return surface
112, 212, 312 second reflection surface
120, 220, 320 light source unit
121, 221, 321 substrate board
122, 222, 322 LED element
123, 223, 323 lens
124, 224, 324 window
211b, 311b preliminary reflection surface
312a reflection direction regulating surface
500 water purifier
510 case
520 partition
530 first lid
540 second lid
550 water-purifying cartridge

The invention claimed is:

1. A sterilization device, comprising:
 a housing having a flow passage of a fluid that is to be sterilized; and
 a light source being disposed in the housing to irradiate ultraviolet light into the flow passage, wherein
 an inner wall surface of the flow passage has a pair of reflection surfaces which direct the ultraviolet light irradiated from the light source from one side of the flow passage to another side thereof while reflecting the ultraviolet light a plurality of times; and
 a return surface disposed within the flow passage and that is composed of a surface that is perpendicular to an optical axis of the light which has been reflected a plurality of times from the one side to the other side, and returns the light toward its original direction is formed on a side of one of the pair of reflection surfaces.

2. The sterilization device according to claim 1, wherein the return surface is a planar surface and an angle between the return surface and one of the pair of reflection surfaces from which the return surface extends is an obtuse angle.

* * * * *